United States Patent [19]
Lau et al.

[11] Patent Number: 5,151,348
[45] Date of Patent: Sep. 29, 1992

[54] ENZYME-LINKED IMMUNOASSAY FOR MEASUREMENT OF CYCLOSPORIN A LEVELS IN WHOLE BLOOD SAMPLES

[75] Inventors: Hon-Peng P. Lau, Hockessin, Del.; Warren K. Miller, Lincoln University, Pa.

[73] Assignee: E.I. du Pont de Nemours and Company, Wilmington, Del.

[21] Appl. No.: 288,912

[22] Filed: Dec. 23, 1988

[51] Int. Cl.$^5$ .................. C12Q 1/00; G01N 33/543; G01N 33/553; G01N 33/538

[52] U.S. Cl. .................. 435/7.92; 436/525; 436/518; 436/541; 436/178; 436/815; 435/962

[58] Field of Search .............. 435/7.92, 962; 436/525, 436/518, 541, 178, 815

[56] References Cited

U.S. PATENT DOCUMENTS

| | | | |
|---|---|---|---|
| 4,235,960 | 11/1980 | Sasse et al. | 435/7.93 |
| 4,668,622 | 5/1987 | Kuhr et al. | 435/14 |
| 4,727,035 | 2/1988 | Mahoney | 436/518 |

FOREIGN PATENT DOCUMENTS 4037585 4/1986 Australia.

OTHER PUBLICATIONS

Tijssen, P. *Practice and Theory of Enzyme Immuno Assays*, Elsevier, Amsterdam, pp. 188-191, 246-249 (1985).
Mahler et al., *Basic Biological Chemistry*, FIG. 15-4 (1968).
Kaplan et al., *Clinical Chemistry*, p. 631.
Quesniaux et al., "Potential of Monoclonal antibodies to Improve Therapeutic Monitoring of Cyclosporine," Clin Chem 33:32-37 (1987).
Lensmeyer et al., Transplantation, 42(4): 372-376 (1986).
Foxwell et al., Biochimica et Biophysica Acta, 938:447-445 (1988).
Quesniaux et al., Eur. J. Immunol., 17: 1359-1365 (1987).
Agarwal et al., Clin. Chem., 33(4): 481-485 (1987).
Ball et al., Clin. Chem., 34(2): 257-260 (1988).
Sandimmun ®-Kit Product Insert Sheet, Sandoz Ltd.
TDx ® Cyclosporine and Metabolites Whole Blood Assay Information, Abbott Laboratories (1988).
Cyclo-Trac ® SP Whole Blood Radioimmunoassay for Cyclosporine Procuct Insert Sheet, Incstar.
Beresini, M., EMIT ® Cyclosporine Assay for Whole Blood Samples on the COBAS MIRA Analyzer, Poster Presentation at the AACC/ICCC Meeting (1990).

*Primary Examiner*—Christine Nucker
*Assistant Examiner*—M. P. Woodward
*Attorney, Agent, or Firm*—Roseanne R. Duffy

[57] ABSTRACT

An enzyme-linked immunoassay for the determination of cyclosporin A levels in whole blood samples is provided based on the utilization of $\beta$-D-galactosidase as an enzyme label and chlorophenol red-$\beta$-D-galactopyranoside or resorufin-$\beta$-D-galactopyranoside as a $\beta$-D-galactosidase substrate.

4 Claims, No Drawings

ENZYME-LINKED IMMUNOASSAY FOR MEASUREMENT OF CYCLOSPORIN A LEVELS IN WHOLE BLOOD SAMPLES

TECHNICAL FIELD

This invention relates to the measurement of cyclosporin A levels in whole blood samples.

BACKGROUND ART

Cyclosporin A is a potent immunosuppressive agent which has been successful in prolonging the survival of kidney, liver and heart allogeneic transplants in humans. Cyclosporin A has been demonstrated to suppress some humoral immunity and, to a greater extent, cell-mediated reactions such as allograft rejection and delayed hypersensitivity. Other cyclosporins, such as cyclosporin G, have also been used as immunosuppressive agents, but are not as widely used as cyclosporin A. High doses of cyclosporin A can cause hepatotoxicity and nephrotoxicity and low doses can leas to possible organ rejection. For these reasons, patients receiving cyclosporin A should be monitored at repeated intervals for cyclosporin A blood levels and subsequent dose adjustments should be made.

In blood, cyclosporin A partitions into red blood cells. Partitioning of cyclosporin A increases as the temperature of blood decreases from body temperature to room temperature. Therefore, to eliminate analytical variability due to time and temperature equilibration, it is advantageous to perform determinations of cyclosporin A blood levels on whole blood samples. Currently, cyclosporin A levels in whole blood samples are determined using radioimmunoassays and high performance liquid chromatography (HPLC). Radioimmunoassays are less advantageous than other immunoassays, such as enzyme-linked immunoassays, because radioimmunoassays require the use of a radioisotope which poses numerous problems associated with handling, storage, and disposal. HPLC is less advantageous than other assays because it requires laborious procedures, such as solvent extraction of cyclosporin A. There have been no cyclosporin A non-radiometric immunoassays described which can be performed directly on whole blood samples.

Enzyme-linked immunoassays have achieved widespread use for the measurement of clinically important analytes. There are many different types of enzyme-linked immunoassays, such as sandwich immunoassays and competitive and noncompetitive heterogeneous immunoassays. Enzyme-linked immunoassays often utilize an enzyme-labeled antibody specific for the analyte of interest. the enzyme-labeled antibody binds to an analyte of interest in a sample and the enzymatic activity of either the bound enzyme-labeled antibody or the free enzyme-labeled antibody is measured by reacting the enzyme with a substrate to produce a detectable chromophore. Affinity columns containing immobilized analyte are often used to separate the free labeled antibody from the bound labeled antibody so that the enzymatic activity of the bound labeled antibody can be measured. Virtually any enzyme that can be coupled to an antibody and can react with a substrate to produce a detectable chromophore can be used in enzyme-linked immunoassays.

An enzyme-linked immunoassay which is to be performed on whole blood samples has unique requirements for selection of enzyme label and enzyme substrate. Since a whole blood sample can contain lysed red blood cells, an enzyme label used in an enzyme-linked immunoassay performed on whole blood samples cannot be endogenous to red blood cells. The enzyme $\beta$-D-galactosidase is not endogenous to red blood cells and is a suitable enzyme label for an enzyme-linked immunoassay performed on whole blood samples.

Red blood cells contain heme, which has an intense absorption peak at 405 nm, known as the Soret band. The absorbance peak at 405 nm is so intense that the measurement of absorbance of a 10 $\mu$L whole blood sample diluted 500-fold would be beyond the capacity of a conventional spectrophotometer. Therefore, a suitable $\beta$-D-galactosidase substrate for use in an enzyme-linked immunoassay performed on whole blood samples should produce a chromophore which does not absorb at or near 405 nm since the interference from the Soret band would be too great. A $\beta$-D-galactosidase substrate most commonly used in enzyme-linked immunoassays is o-nitrophenyl-$\beta$-D-galactopyranoside (ONPG). However, since ONPG produces a chromophore which absorbs at 405 nm, it is not a suitable $\beta$-D-galactosidase substrate for use in an enzyme-linked immunoassay performed on whole blood samples.

Two classes of $\beta$-D-galactosidase substrates producing chromophores which absorb in the visible range, approximately 560 nm to 590 nm, are phenolsulphonphthaleinyl-$\beta$-D-galactosides (U.S. Pat. No. 4,668,622, issued May 26, 1987, to Kuhr et al.) and glycosides of resorufin derivatives (DE 3411574, issued Oct. 3, 1985). These substrates are described as being useful for enzyme immunoassays in which $\beta$-D-galactosidase is used as an indicator enzyme. While no interference in absorbance measurement would be caused by the Soret band, oxyhemoglobin, another consitituent of red blood cells, has an absorbance peak at 577 nm. Therefore, the two above-identified classes of $\beta$-D-galactosidase substrates are not expected to be suitable for an enzyme-linked immunoassay performed on whole blood samples because of interference from oxyhemoglobin.

There remains a need for an enzyme-linked immunoassay for the direct and rapid measurement of cyclosporin A levels in whole blood samples.

SUMMARY OF THE INVENTION

The enzyme-linked immunoassay of this invention for the measurement of cyclosporin A levels in whole blood samples comprises the steps of:

(a) lysing red blood cells in a sample of whole blood containing cyclosporin A;

(b) contacting the lysed whole blood sample with excess $\beta$-D-galactosidase-labeled anti-cyclosporin antibody to form a labeled antibody-cyclosporin A complex;

(c) separating unbound antibody from the complex by contacting the mixture formed in step (b) with a solid phase comprising cyclosporin immobilized on a solid support; and (d) determining the amount of the $\beta$-D-galactosidase label in the complex as a measure of cyclosporin A by adding a $\beta$-D-galactosidase substrate selected from the group consisting of chlorophenol red-$\beta$-D-galactopyranoside and resorufin-$\beta$-D-galactopyranoside.

DESCRIPTION OF THE INVENTION

The enzyme-linked immunoassay of this invention is useful for measuring cyclosporin A levels in whole blood samples of patients receiving cyclosporin A. Monitoring of cyclosporin A blood levels and subsequent cyclosporin A dosage adjustment are necessary to prevent toxic effects caused by high cyclosporin A blood levels and to prevent organ rejection caused by low cyclosporin A blood levels.

Unexpectedly, it has been found that an enzyme-linked immunoassay for measurement of cyclosporin A in whole blood samples can be performed by using β-D-galactosidase as an enzyme label and chlorophenol red-β-D-galactopyranoside (CPRG) or resorufin-β-D-galactopyranoside (ReG) as a β-D-galactosidase substrate. These two substrates have been found to have sensitivities so high that the volume of whole blood used as a sample in the immunoassay can be greatly reduced while still maintaining acceptable precision and accuracy. Therefore, even though these substrates produce chromophores which absorb at the same wavelength as oxyhemoglobin, the sample volume can be made to be sufficiently small to minimize oxyhemoglobin absorbance interference.

CPRG and ReG are disclosed among the numerous β-D-galactosidase substrates in U.S. Pat. No. 4,668,622 and DE 3411574. It is believed, however, that the other β-D-galactosidase substrates disclosed in the two above-identified patents are not as sensitive as CPRG and ReG and, therefore, an enzyme-linked immunoassay for use on whole blood samples utilizing such substrates can require a larger whole blood sample volume. Since a larger sample volume results in higher absorbance interference from oxyhemoglobin, the immunoassay cannot be performed accurately without a means for reducing such absorbance interference. One means for reducing the absorbance interference is to include potassium ferricyanide in the immunoassay to convert oxyhemoglobin to methemoglobin, which has a low, broad absorbance peak between 550 and 600 nm. The advantage of using CPRG or ReG as β-D-galactosidase substrates in the enzyme-linked immunoassay of this invention is that there is no need for the use of potassium ferricyanide since both substrates are sufficiently sensitive to allow the use of small sample volumes.

The enzyme-linked immunoassay of the present invention is performed by contacting a lysed whole blood sample containing cyclosporin A with excess β-D-galactosidase-labeled anti-cyclosporin antibody to form a reaction mixture containing a complex of cyclosporin A with labeled antibody and free labeled antibody, separating free antibody from the reaction mixture by contacting the reaction mixture with a solid phase comprising an immobilized cyclosporin on a solid support, separating the solid phase from the liquid phase, and measuring the amount of the bound β-D-galactosidase label in the liquid phase by adding to the liquid phase CPRG or ReG as a β-D-galactosidase substrate.

Specifically, the red blood cells of a whole blood sample containing cyclosporin A must be lysed to release cyclosporin A. Red blood cell lysis can be accomplished by many methods, such as sonication, detergent lysis and distilled water lysis. The lytic agent chosen should be compatible with the β-D-galactosidase-labeled anti-cyclosporin antibody. Although some detergents can denature β-D-galactosidase, it has been found that by using CPRG and ReG as β-D-galactosidase substrates, the sample volume can be made to be sufficiently small to minimize the denaturing effect of the detergent. The preferred lysis method uses distilled water.

After lysis, a reaction mixture is formed by contacting the lysed whole blood sample with excess β-D-galactosidase-labeled anti-cyclosporin antibody and incubating the reaction mixture for a time and at a temperature sufficient to permit the labeled antibody to form a complex with all of the cyclosporin A in the sample. This usually takes 10–30 minutes at room temperature. Anti-cyclosporin antibody can be obtained commercially or prepared by known methods. The anti-cyclosporin antibody can be polyclonal or monoclonal. A monoclonal anti-cyclosporin antibody specific for cyclosporin A is preferred. The anti-cyclosporin antibody is labeled with β-D-galactosidase by standard conjugation techniques.

The unbound β-D-galactosidase-labeled anti-cyclosporin antibody is separated from the reaction mixture by contacting the reaction mixture with a solid phase comprising cyclosporin immobilized on a solid support for a time sufficient to permit the unbound labeled antibody to form a complex with the immobilized cyclosporin. This usually occurs in approximately one minute. Any cyclosporin which can be immobilized on a solid support can be utilized in the enzyme-linked immunoassay of the present invention so long as such cyclosporin is capable of forming a complex with the anti-cyclosporin antibody. Cyclosporin C is preferred for the ease with which it can be immobilized on a solid support.

The immobilization of cyclosporin can be accomplished by a number of known immobilization techniques. The preferred immobilization technique for cyclosporin C is to derivatize cyclosporin C to cyclosporin C-hemisuccinate and couple it to a protein, such as albumin or globulin, which can be covalently coupled to a solid support.

Cyclosporin can be immobilized on a variety of solid supports. The solid support is chosen for its flow characteristics and can include beaded dextran, beaded agarose, polyacrylamide, or glass. A preferred solid support useful in the enzyme-linked immunoassay of this invention is described in applicants' assignee's, E.I. du Pont de Nemours and Company, copending patent application Ser. No. 07/074,242, filed Jul. 16, 1987, incorporated herein by reference.

The preferred solid support comprises a beaded dextran chromatographic column containing an immobilized flocculating agent and trapped stabilized chromium dioxide particles having cyclosporin bound to their surfaces. Any flocculating agent can be used, but polyethyleneimine (PEI) is preferred. PEI can be attached to beaded dextran having a diameter of approximately 40 to 120 microns, such as Sephadex G-10 resin, by simple adsorption. This can be accomplished by soaking Sephadex G-10 resin in a 1% solution of PEI in a 0.15M sodium phosphate buffer.

The stabilized chromium dioxide particles useful in the preferred solid support are those described in U.S. Pat. No. 4,661,408, issued Apr. 28, 1987, incorporated herein by reference. These particles consist of a core of rutile chromium dioxide which has been extensively surface reduced, coated with alumina, further coated with silica containing borate and still further coated with a silane to which is attached cyclosporin. These particles have large surface areas, 40–100 $m^2/g$, are stable in aqueous solution and can be readily coupled to cyclosporin. The particles coupled to cyclosporin are eluted through the beaded dextran chromatographic column containing immobilized flocculating agent and become trapped within the column. It has been found that by using the preferred solid support in the enzyme-linked immunoassay of this invention, the amount of cyclosporin required to remove unbound labeled anti-cyclosporin antibody is reduced by over 300-fold compared to the amount required when using beaded dextran alone as a solid support.

The solid phase is separated from the liquid phase by standard separation techniques. The preferred separation technique is to elute the liquid phase through the preferred solid support described above.

The amount of cyclosporin A is determined by measuring the amount of the bound $\beta$-D-galactosidase label in the liquid phase. The amount of bound $\beta$-D-galactosidase is determined by adding to the liquid phase either CPRG or ReG as a $\beta$-D-galactosidase substrate and measuring spectrophotometrically the amount of chromophore produced at 577 nm.

The enzyme-linked immunoassay of this invention can be performed manually or it can be adapted to a variety of automated or semi-automated instrumentation, such as the aca® discrete clinical analyzer (a registered trademark of E.I. du Pont de Nemours and Company, Inc., Wilmington, Del.). In performing the assay on an aca® analyzer, a whole blood sample is first lysed and preincubated with excess $\beta$-D-galactosidase-labeled anti-cyclosporin antibody outside the instrument. A known volume of this mixture is automatically injected into an analytical test pack (described in U.S. Pat. No. Re. 29,725 to Johnson et al., reissued Aug. 8, 1978, and incorporated herein by reference) in the filling station of the instrument, followed by a volume of buffer sufficient to bring the final in-pack volume to approximately 5 mL. The sample mixture percolates through a column of cyclosporin immobilized on a porous support located in the pack header and is eluted directly into the pack. The eluted fraction contains $\beta$-D-galactosidase-labeled anti-cyclosporin antibody complexed with cyclosporin A from the whole blood sample. The pack is automatically processed at 37° C. with the addition of CPRG or ReG immediately preceding the absorbance measurements at 577 nm.

EXAMPLE

Measurement of Cyclosporin A in Whole Blood Samples

A. Immobilization of Cyclosporin on Solid Support

Two hundred and fifty mg of cyclosporin C (Sandoz Ltd.), 144 mg of 4-dimethylaminopyridine and 70 mg of succinic anhydride were mixed in 0.8 mL of anhydrous pyridine. This mixture was heated at approximately 75° C. for 4 hours and approximately 30 mL of methylene chloride was then added to the mixture. The resulting mixture was washed three times with 15 mL of 1N hydrochloric acid per wash and then washed two times with 20 mL of water per wash. The organic layer was removed, mixed with 5 g of anhydrous sodium sulfate and evaporated to dryness. The resulting solid, 250 mg, was dissolved in 12.5 mL of anhydrous acetonitrile to form a 20 mg/mL cyclosporin C-hemisuccinate solution.

To 2 mL of the cyclosporin C-hemisuccinate solution formed above was added 14 mg of 2-fluoro-1-methyl-pyridinium toluene 4-sulfonate (Aldrich Chemicals) and 8 $\mu$L of triethylamine. The resulting mixture was incubated at room temperature for one hour and 200 mg of bovine globulin in 50 mL of 0.1M sodium carbonate buffer (pH 9.5) was added, forming a cloudy solution. The solution was stirred on a magnetic stirrer plate at room temperature for approximately 18 hours. The solution was dialyzed against phosphate buffer saline (PBS, 10 mM sodium phosphate, 0.9% sodium chloride, pH 7.0) and diluted to 0.3 mg/mL bovine globulin with PBS, based on a starting bovine globulin concentration of 200 mg/52 mL.

Chromium dioxide particles were prepared as described in U.S. Pat. No. 4,661,408. To 250 mL of a chromium dioxide particle suspension (5% w/v of chromium dioxide particles in 10 mM phosphate buffer) was added 250 mL of the cyclosporin C-hemisuccinate-globulin solution prepared above. The mixture was stirred for approximately 18 hours, washed eight times with 1 L of wash buffer (10 mM TRIS, 150 mM sodium chloride, 0.05% Tween 20 and 0.3% chloroacetamide) per wash and two times with 1 L of a 0.1% BSA solution in 10 mM phosphate buffer per wash.

One hundred grams of Sephadex G-10 (Pharmacia Fine Chemicals) was mixed with 500 mL of 0.15M sodium phosphate buffer (pH 7.8) containing 5 g of PEI at room temperature for approximately 18 hours. Unbound PEI was removed by washing the mixture five times with 500 mL of distilled water per wash and two times with 500 mL of 0.15M sodium phosphate per wash.

Twenty-five mL of the cyclosporin C-hemisuccinate-globulin-chromium dioxide particle mixture prepared above was mixed thoroughly with 100 mL of PEI-Sephadex G-10 and 100 mL of 0.15M sodium phosphate buffer. The mixture was packed into aca® discrete clinical analyzer analytical columns (0.5×8 cm, 1.8 mL per column). The columns in turn were placed in the headers of aca® discrete clinical analyzer test packs containing 100 $\mu$L of a 150 mg/mL solution of CPRG in water or, alternatively, 180 $\mu$L of a 16 mg/mL solution of ReG in n-methylpyrrolidone which had been diluted 1:2 with water.

B. Enzyme-Linked Immunoassay for Measurement of Cyclosporin A in Whole Blood Samples Using CPRG and ReG as $\beta$-D-Galactosidase Substrates Whole blood cyclosporin A samples of various concentrations were prepared by adding cyclosporin A (Sandoz Ltd.) to whole blood to achieve cyclosporin A concentrations of 0, 100, 300, 500, and 1000 ng/mL. These samples were divided into two sets, one for each of CPRG and ReG, and processed as follows. Red blood cells were lysed by adding 200 $\mu$L of distilled water to 50 $\mu$L of each sample. A 50-$\mu$L aliquot of each lysate was then added to 50 $\mu$L of $\beta$-D-galactosidase-labeled anti-cyclosporin antibody conjugate reagent (Sandoz Ltd.) and incubated for 20 minutes at room temperature. After incubation, each sample lysate-antibody mixture was automatically injected into an aca® discrete clinical analyzer analytical test pack and eluted through the column in the pack header. Each sample was followed by 2 mL of 0.15M sodium phosphate, pH 7.8. The column flow rate was 34 $\mu$L/sec. The pack was then filled at needle position 2 (which bypasses the column) with an additional 2.9 mL of water. Substrate (either CPRG or ReG) was released from breaker/mixer II approximately 3.7 minutes later. Absorbance was measured at 577 nm, 29 and 46 sec after addition of substrate. The absorbance rates, expressed in mA/min, are shown in the Table for each cyclosporin A level in whole blood:

TABLE

| Cyclosporin A | Absorbance (mA/min at 577 nm) | |
|---|---|---|
| (ng/mL whole blood) | CPRG | ReG |
| 0 | 63 | 36 |
| 100 | 122 | 52 |
| 300 | 208 | 110 |
| 500 | 234 | 118 |
| 1000 | 262 | 141 |

As can be seen from the Table, absorbance rates (mA/min) were proportional to cyclosporin A levels in whole blood samples when CPRG and ReG were used as $\beta$-D-galactosidase substrates. Although CPRG exhibited greater sensitivity as evidenced by the higher absorbance rate per ng/mL of cyclosporin A, both substrates exhibited sensitivities suitable for precise and accurate measurement of cyclosporin A levels in whole blood samples using conventional spectrophotometers.

We claim:

1. An enzyme-linked immunoassay for the measurement of cyclosporin A levels in whole blood samples comprising the steps of:

(a) lysing red blood cells in a sample of whole blood containing cyclosporin A;

(b) contacting the lysed whole blood sample with excess $\beta$-D-galactosidase-labeled anti-cyclosporin antibody to form a labeled antibody-cyclosporin A complex;

(c) separating unbound antibody from the complex by contacting the mixture formed in step (b) with a solid phase comprising cyclosporin immobilized on a solid support; and (d) determining the amount the of $\beta$-D-galactosidase label in the complex as a measure of cyclosporin A by adding a $\beta$-D-galactosidase substrate selected from the group consisting of chlorophenol red-$\beta$-D-galactopyranoside and resorufin-$\beta$-D-galactopyranoside.

2. The immunoassay of claim 1 wherein the immobilized cyclosporin is cyclosporin C.

3. The immunoassay of claim 1 wherein the solid phase is a beaded dextran containing an immobilized flocculating agent and trapped stabilized chromium dioxide particles having cyclosporin bound to their surfaces.

4. The immunoassay of claim 3 wherein the immobilized flocculating agent is polyethyleneimine.

* * * * *